United States Patent [19]
Edwards

[11] Patent Number: 6,024,743
[45] Date of Patent: Feb. 15, 2000

[54] METHOD AND APPARATUS FOR SELECTIVE TREATMENT OF THE UTERUS

[76] Inventor: Stuart D. Edwards, 658 Westridge Dr., Portola Valley, Calif. 94028

[21] Appl. No.: 09/018,592

[22] Filed: Feb. 4, 1998

Related U.S. Application Data

[63] Continuation-in-part of application No. 08/731,372, Oct. 11, 1996, which is a continuation-in-part of application No. 08/319,373, Oct. 6, 1994, Pat. No. 5,575,788, which is a continuation-in-part of application No. 08/286,862, Aug. 4, 1994, Pat. No. 5,558,672, which is a continuation-in-part of application No. 08/272,162, Jul. 7, 1994, Pat. No. 5,569,241, which is a continuation-in-part of application No. 08/265,459, Jun. 24, 1994, Pat. No. 5,505,730.

[51] Int. Cl.$^7$ .................................................. A61B 17/39
[52] U.S. Cl. ................................ 606/42; 606/41; 606/31; 607/102; 607/105
[58] Field of Search .................................. 606/27–31, 41, 606/42, 191–194, 198; 607/100–105; 604/21, 22, 96–103, 105

[56] References Cited

U.S. PATENT DOCUMENTS

| | | | |
|---|---|---|---|
| 5,019,075 | 5/1991 | Spears et al. | 606/7 |
| 5,047,028 | 9/1991 | Qian | 606/49 |
| 5,084,044 | 1/1992 | Quint | 606/27 |
| 5,232,444 | 8/1993 | Just et al. | 604/96 |
| 5,236,413 | 8/1993 | Feiring | 604/21 |
| 5,292,321 | 3/1994 | Lee | 606/28 |
| 5,542,926 | 8/1996 | Crocker | 604/102 |
| 5,562,720 | 10/1996 | Stern et al. | 607/98 |

Primary Examiner—Michael Peffley
Attorney, Agent, or Firm—Wilson Sonsini Goodrich & Rosati

[57] ABSTRACT

An apparatus to treat an uterus includes an expandable member configured to be positioned in a uterine cavity in a non-deployed, state, receive an expansion media and extend to a deployed state. At least a portion of the expansion media is released through an expandable member exterior surface. Upon removal of at least a portion of the expansion from the expandable member, the expandable member contracts to a non-deployed state. An energy delivery device is coupled to the expandable member. A frame member is positionable in the interior of the expandable member. The frame member includes a first arm coupled to a second arm. The frame member has a non-deployed state and a deployed state where the first and second arms distend away from each other. Each of the expandable member and the frame member have a non-deployed size to be introduced into the uterine cavity. A first thermal sensor member is coupled to the first arm and configured to be advanced from the first arm in the frame member expanded state into an interior of the uterus.

53 Claims, 14 Drawing Sheets

| TIME | Temp 1 | Temp 2 | Temp 3 | Imp. |
|---|---|---|---|---|
| 0.0 | 24.4 | 24.4 | 24.5 | 0 |
| 0.5 | 26.0 | 39.0 | 27.0 | 41 |
| 1.0 | 27.0 | 48.0 | 32.0 | 33 |
| 1.5 | 32.0 | 65.0 | 41.0 | 33 |
| 2.0 | 35.0 | 72.0 | 46.0 | 33 |
| 2.5 | 39.0 | 81.0 | 51.0 | 33 |
| 3.0 | 41.3 | 83.0 | 53.0 | 33 |
| 3.5 | 45.0 | 91.0 | 57.0 | 34 |
| 4.0 | 47.0 | 84.0 | 56.0 | 33 |
| 4.5 | 49.0 | 85.0 | 57.0 | 33 |
| 5.0 | 49.0 | 85.5 | 58.0 | 33 |

| TIME | Temp 1 | Temp 2 | Temp 3 | Imp. |
|---|---|---|---|---|
| 0.0 | 27.0 | 77.8 | 77.9 | 0 |
| 0.5 | 29.0 | 48.0 | 30.5 | 32 |
| 1.0 | 32.0 | 52.0 | 36.0 | 32 |
| 1.5 | 36.0 | 70.0 | 48.0 | 32 |
| 2.0 | 69.0 | 72.0 | 52.0 | 32 |
| 2.5 | 44.0 | 49.0 | 56.0 | 32 |
| 3.0 | 48.0 | 84.0 | 58.0 | 32 |
| 3.5 | 51.0 | 84.0 | 58.5 | 33 |
| 4.0 | 52.0 | 79.2 | 56.3 | 33 |
| 4.5 | 52.2 | 76.6 | 55.5 | 33 |
| 5.0 | 52.1 | 75.4 | 54.2 | 33 |

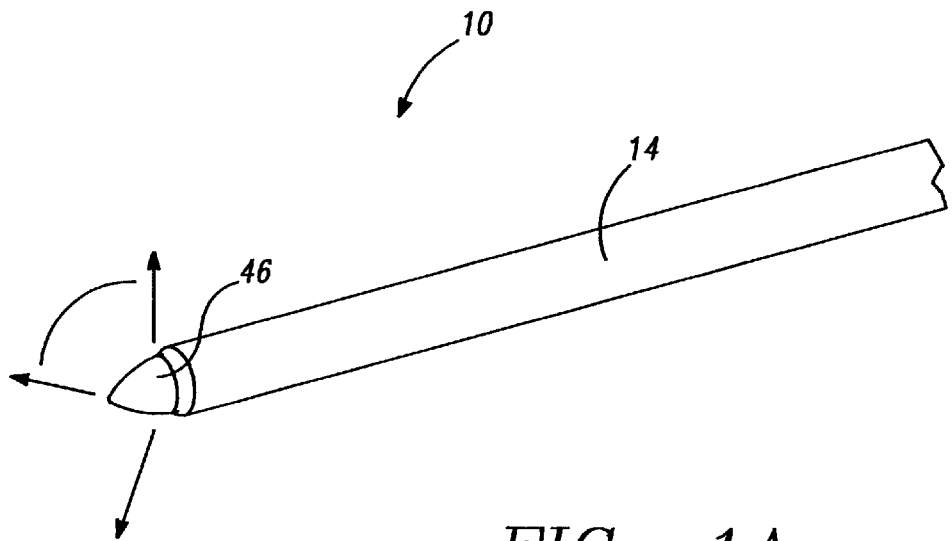
*FIG.—1A*
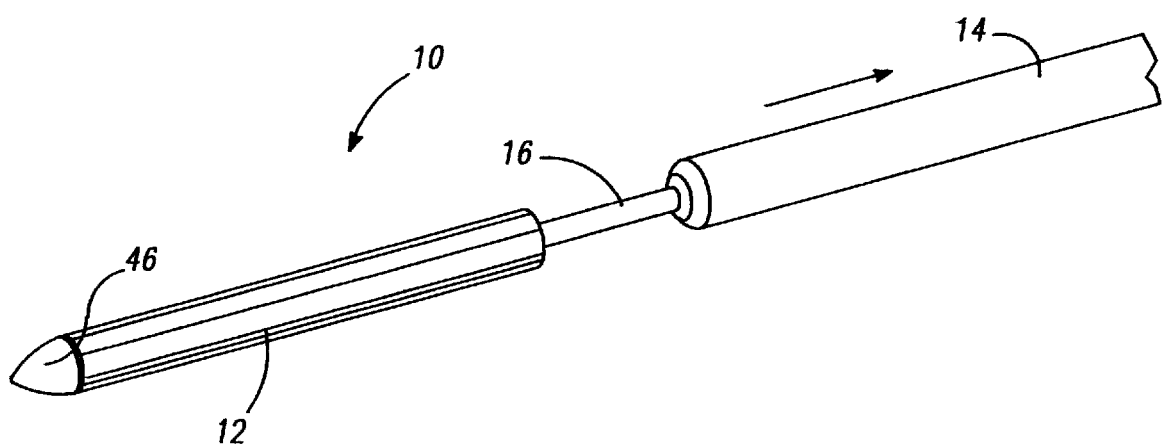
*FIG.—1B*

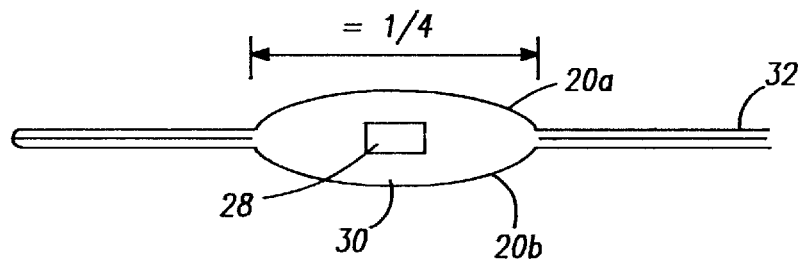
FIG.—5A
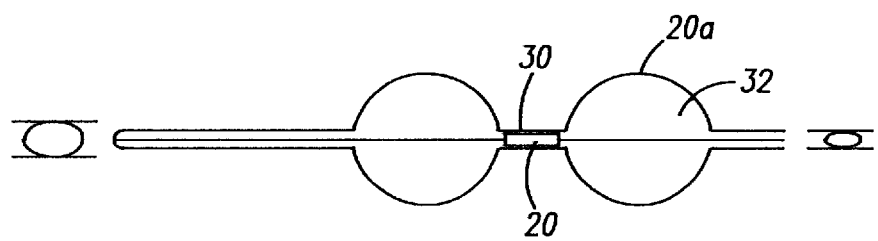
FIG.—5B
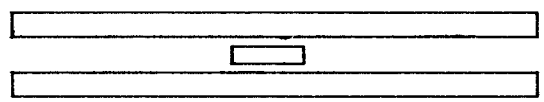
FIG.—5C
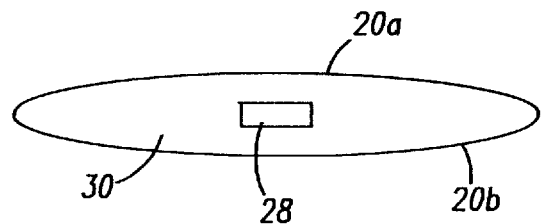
FIG.—5D

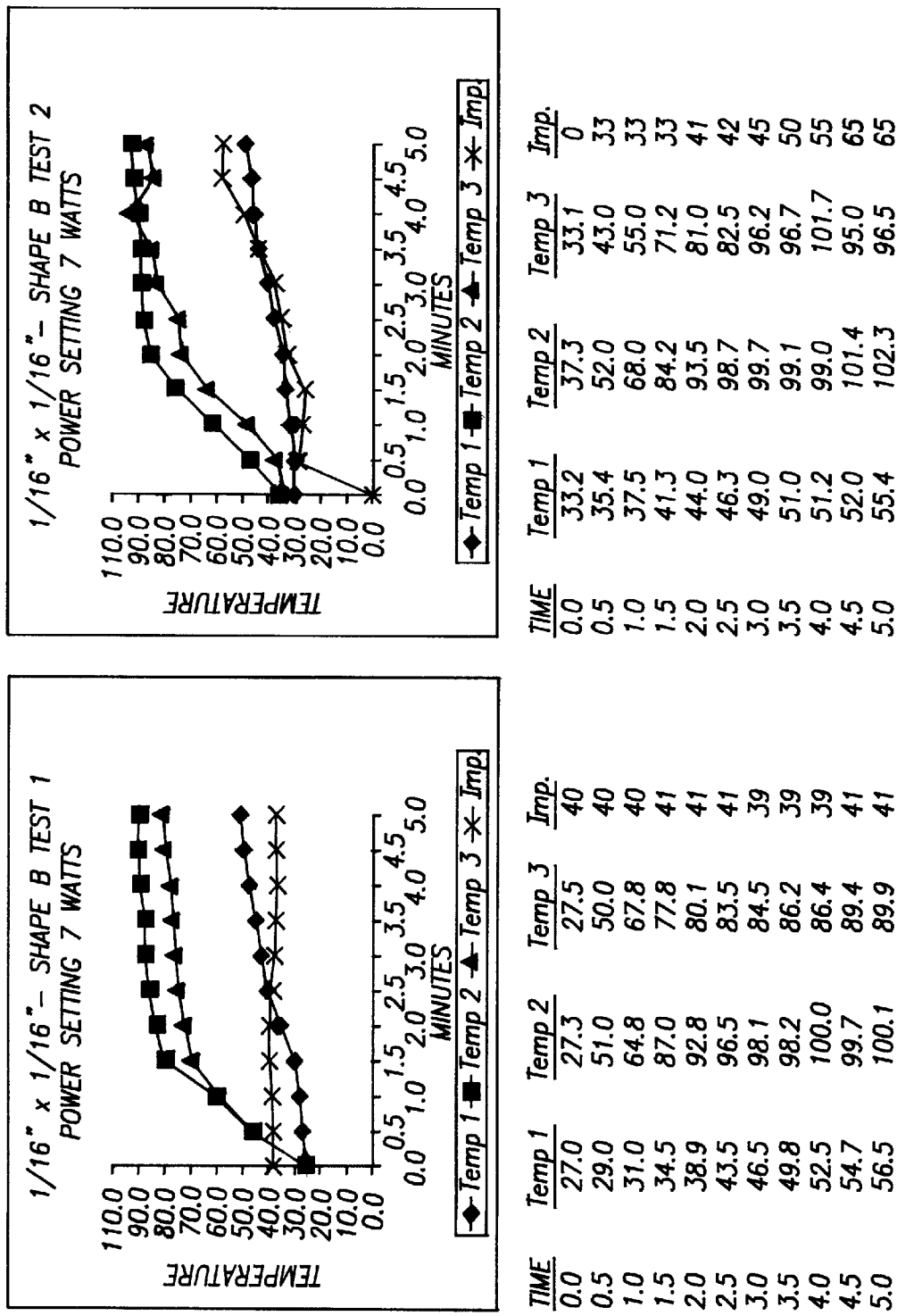

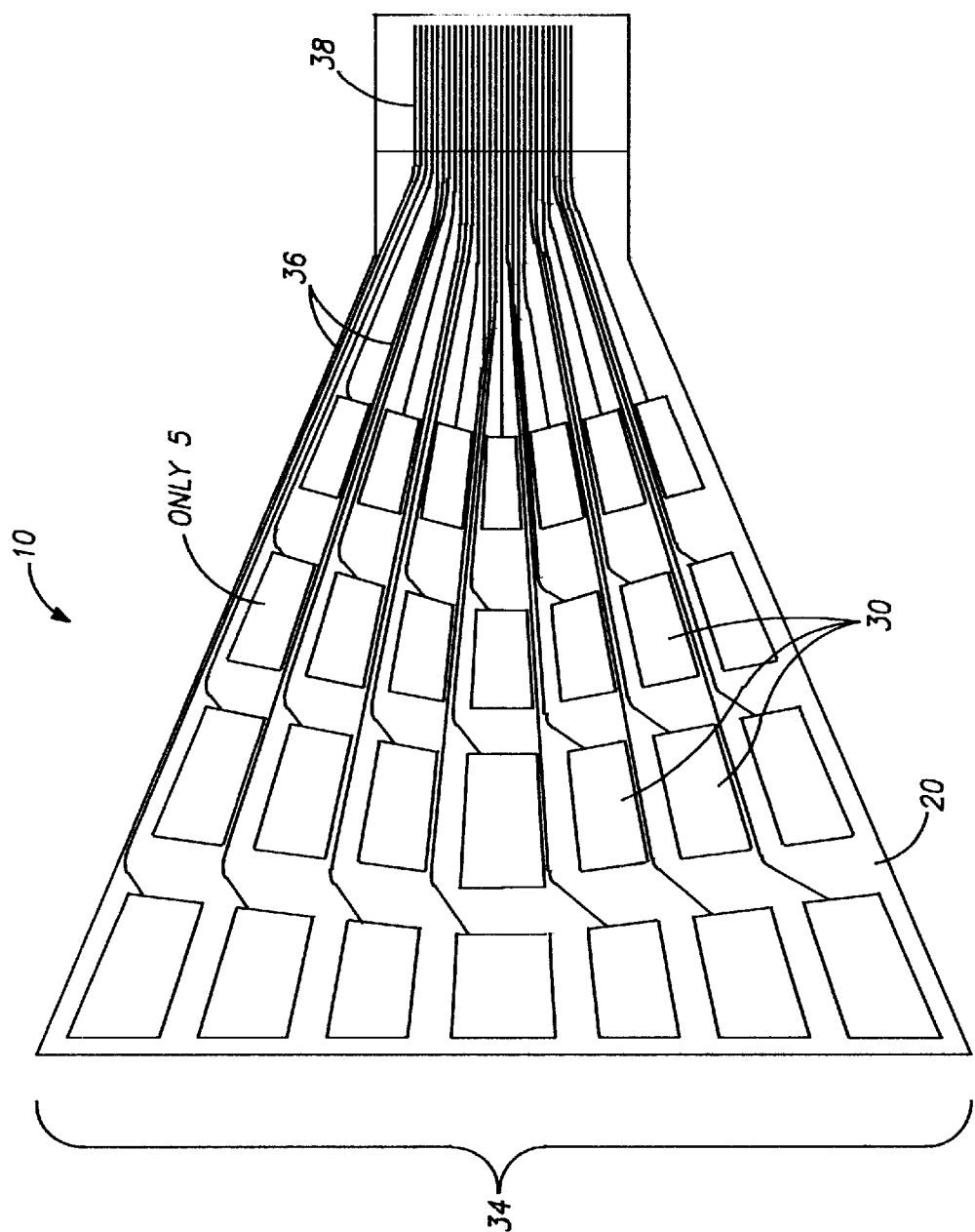

METHOD AND APPARATUS FOR SELECTIVE TREATMENT OF THE UTERUS

CROSS-REFERENCE TO RELATED APPLICATIONS

This application is a continuation-in-part of U.S. patent application Ser. No. 08/731,372, filed Oct. 11, 1996, which is a continuation-in-part of U.S. patent application Ser. No. 08/319,373, filed Oct. 6, 1994, now U.S. Pat. No. 5,575,788, which is a continuation-in-part of U.S. application Ser. No. 08/286,862, filed Aug. 4, 1994, now U.S. Pat. No. 5,558,672 which is a continuation-in-part of U.S. patent application Ser. No. 08/272,162, filed Jul. 7, 1994, now U.S. Pat. No. 5,569,241, which is a continuation-in-part of U.S. patent application Ser. No. 08/265,459, filed Jun. 24, 1994, now U.S. Pat. No. 5,505,730, all of which are incorporated by reference.

BACKGROUND OF THE INVENTION

1. Field of the Invention

This invention relates generally to a method and apparatus to controllably create cell necrosis of at least a portion of the uterus, and more particularly to method and apparatus to create selective cell necrosis of target sites of the uterus.

2. Description of Related Art

There are a number of body organs and lumens, including but not limited to the uterus, gall bladder, large intestine and the like, that have inner layers which have abnormal conditions. Traditional methods of treatment have included removal of the body organ to treat the abnormal condition, the use of lasers, and the application of a thermal source.

A diseased condition of the uterus, menorrhagia, is defined as excessive menstrual bleeding in the absence of organic pathology. It has no known aetiology and it has been postulated that it is due to an inappropriate exposure of the endometrium to hormones. Menorrhagia is an exceedingly common problem, typically comprising approximately one in five outpatient referrals to gynecological departments. Women suffering severe menorrhagia are at risk from chronic anemia. The first treatment employed may be the administration of drug therapy. A major disadvantage is the need to administer drugs long term, and frequently the beneficial effects are only temporary. Another treatment is hysterectomy.

A number of physical and chemical methods have been tried as alternatives to hysterectomy, including the use of superheated steam, cryotherapy, urea injection and radium packing. The most commonly used methods as an alternative to hysterectomy are, ablation of the endometrium either by using a laser, such as a Nd:YAG laser, or the use of RF energy applied with an electrode.

Laser treatments have provided only limited success. RF is an attractive alternative. In RF heating, a conductive probe is placed within the uterine cavity and an insulated ground-plane electrode or belt is placed around the patient's midriff. RF energy is applied to the thermal probe with the external belt electrode acting as the return arm of the circuit. The electrical load presented by the RF thermal probe, patient, and external belt is matched to the output of the RF generator via a tuning unit, to form a series resonant circuit. Once tuned, the majority of the power applied to the probe is deposited into the endometrium as heat.

Current flows primarily capacitively, and an electric field is set up around the active tip of the probe. Tissue lying within the field becomes heated because of rapid oscillation of charged particles and locally induced currents.

Prior et al. have reported on the use of RF to treat menorrhagia. Power at 27·12 MHz was delivered to a probe that was placed into the uterine cavity and capacitively coupled to a second electrode consisting of a belt placed around the patient, Prior et al., Int. J. Hyperthermia, 1991, Vol. 7, No. 2, pgs 213 to 220. The active electrode was a 10 mm diameter stainless-steel cylinder with a length of 70 mm. This method, however, did not adequately deliver RF energy to the entire endometrium. Because the endometrium has an irregular surface, it is difficult to deliver sufficient RF energy to the entire structure and effectively treat menorrhagia.

However, it is desirable to have close contact between the RF conductive face and the endometrium. In U.S. Pat. No. 5,277,201 (the "'201 patent") an electroconductive, expandable balloon expands the interior of the uterus and effects electrical contact with the endometrial lining to be destroyed. The device of the '201 patent fails, however, to provide sufficient physical contact with the entire endometrium, and thus the treatment is not complete. Not only is the physical contact with the endometrium unsatisfactory, but the effective delivery of RF energy to the endometrium could be improved.

There is a need to provide a method and apparatus to minimally invasively treat the uterus. There is a another need for a method and apparatus to minimally invasively treat selected sites of the uterus. There is a further need for a method and apparatus to selectively treat endometriosis and/or fibroids. There is yet another need for a method and apparatus to treat the uterus with a relatively large margin of error.

SUMMARY OF THE INVENTION

Accordingly, an object of the invention is to provide a method and apparatus to minimally invasively treat the uterus.

Another object of the invention is to provide a method and apparatus to minimally invasively treated selected sites of the uterus.

A further object of the invention is to provide a method and apparatus to selectively treat endometriosis.

Another object of the invention is to provide a method and apparatus to selectively treat fibroids.

Still another object of the invention is to provide a method and apparatus to treat the uterus with a relatively large margin of error.

Another object of the invention is to provide an easy to use method and apparatus to selectively create cell necrosis in the uterus.

These and other objects of the invention are achieved in an apparatus to treat an uterus. The apparatus includes an expandable member configured to be positioned in a uterine cavity in a non-deployed state, receive an expansion media and extend to a deployed state. At least a portion of the expansion media is released through an expandable member exterior surface. Upon removal of at least a portion of the expansion from the expandable member, the expandable member contracts to a non-deployed state. An energy delivery device is coupled to the expandable member. A frame member is positionable in the interior of the expandable member. The frame member includes a first arm coupled to a second arm. The frame member has a non-deployed state and a deployed state where the first and second arms distend away from each other. Each of the expandable member and the frame member have a non-deployed size to be introduced into the uterine cavity. A first thermal sensor member is coupled to the first arm and configured to be advanced from the first arm in the frame member expanded state into an interior of the uterus.

In another embodiment, a method for treating a uterus provides a treatment apparatus including an expandable member, an energy delivery device coupled to the expandable member, a frame member positionable in the interior of the expandable member and a first thermal sensor member coupled to the frame member. At least a portion of the expandable member is introduced into an uterine cavity. The first thermal sensor is introduced into a selected site of the uterus. Energy is delivered from the energy delivery to a selected site of the uterus and create controlled cell necrosis. The expandable member is then removed from the uterine cavity.

DESCRIPTION OF THE DRAWINGS

FIG. 1(a) is a perspective view of a cell necrosis apparatus of the invention housed in an introducer sleeve and includes viewing optics.

FIG. 1(b) is a perspective view of a cell necrosis apparatus of the invention in a non-deployed position as the introducer sleeve is withdrawn.

FIG. 5(a) is a cross-sectional view of the conforming member made of an open cell foam material. Two pieces of foam are sealed to create a zone, or pocket, of electrolytic solution around an RF electrode.

FIG. 5(b) is a cross-sectional view of the conforming member made of an open cell foam material. Two pieces of foam are sealed at the electrode, creating the zone that comprises an RF electrode and electrolytic solution which remains in the zone a longer time than the electrolytic solution ill non-zone regions of the conforming member.

FIGS. 5(c)–5(d) are cross-sectional views of two layers of an open cell foam that are jointed with an RF electrode disposed between the two layers, forming a zone. The zone has a lower porosity rate than non-zone areas. Included in the zone is electrolytic solution, which together with the RF electrode create a larger electrode.

FIGS. 7(a)–7(b) are graphs and tables of measured temperatures of zone and adjacent non-zone sections of the cell necrosis apparatus illustrated in FIG. 5(b).

FIG. 8 is a cross-sectional view of a multiplicity of zones in the conforming member.

Housed in the introducer sheath are viewing and illumination fibers, a tension wire, an RF cable, an ultrasound cable and an electrolytic solution tube.

Figure 12:
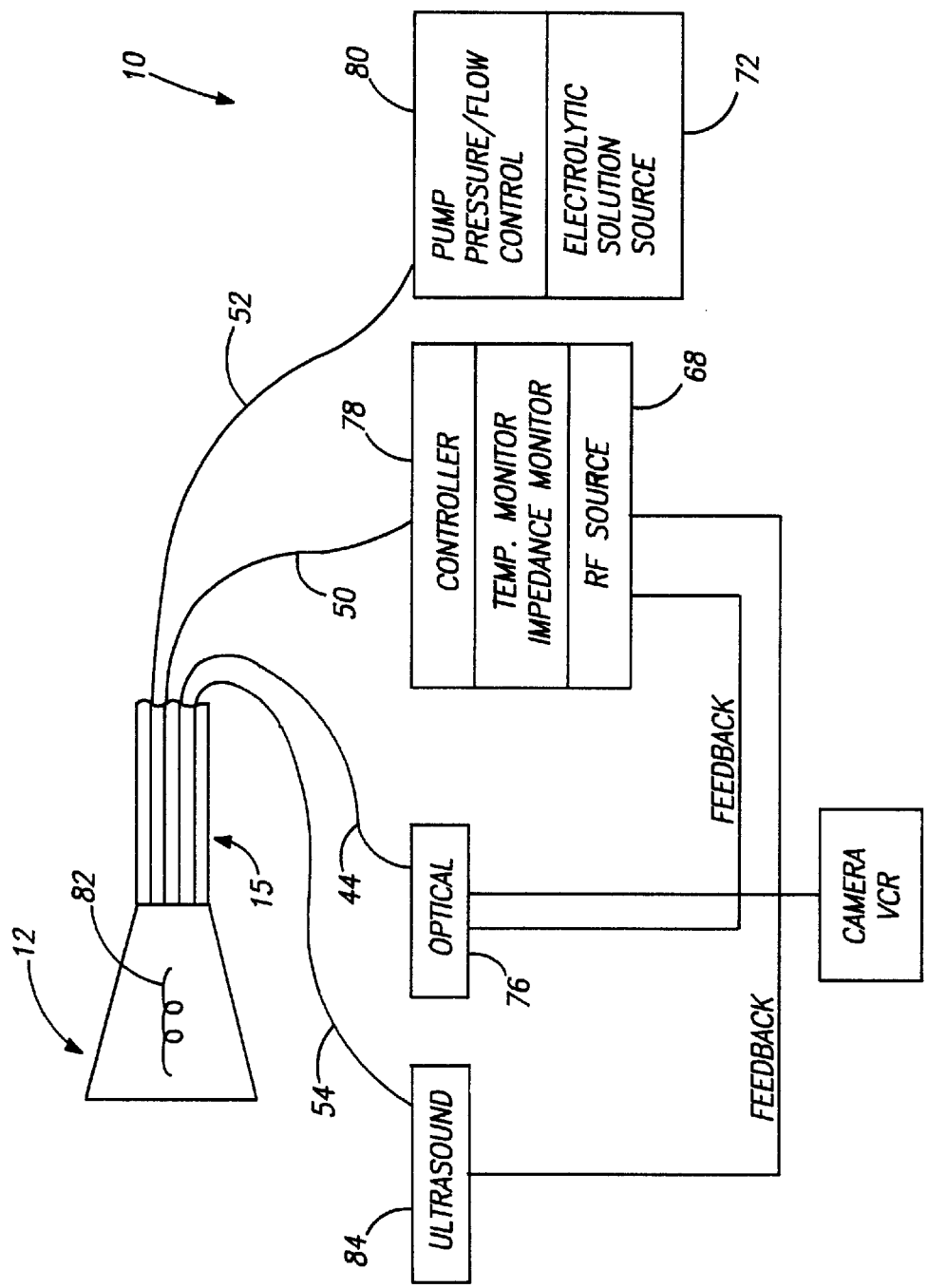

FIG. 12 is a representative block diagram of the invention showing the light, RF, ultrasound and electrolytic sources and their relationships to the expandable member.

Figure 13:
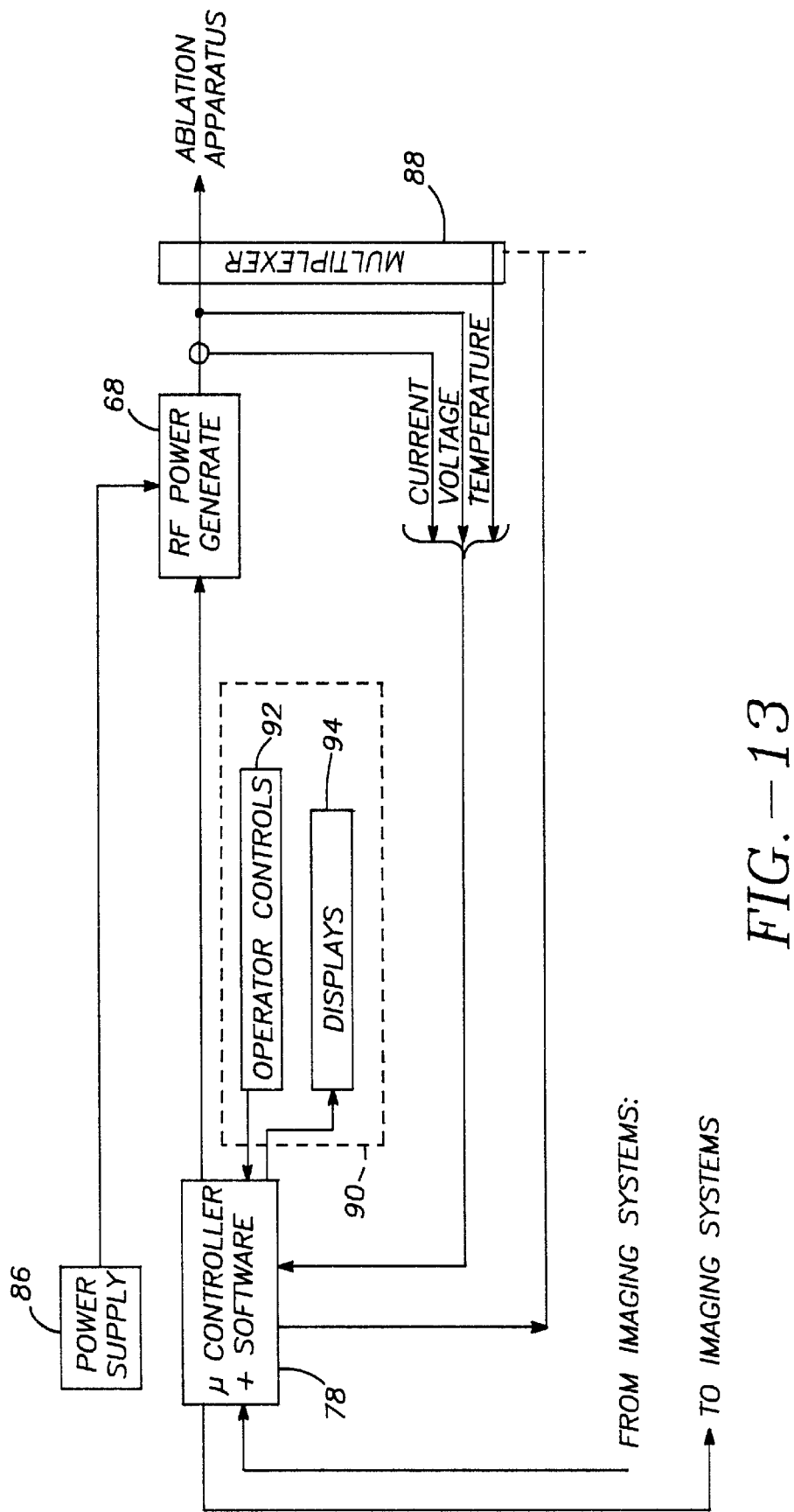

FIG. 13 is a block diagram of a cell necrosis apparatus of the invention that includes a controller and multiplexer.

Figure 14:
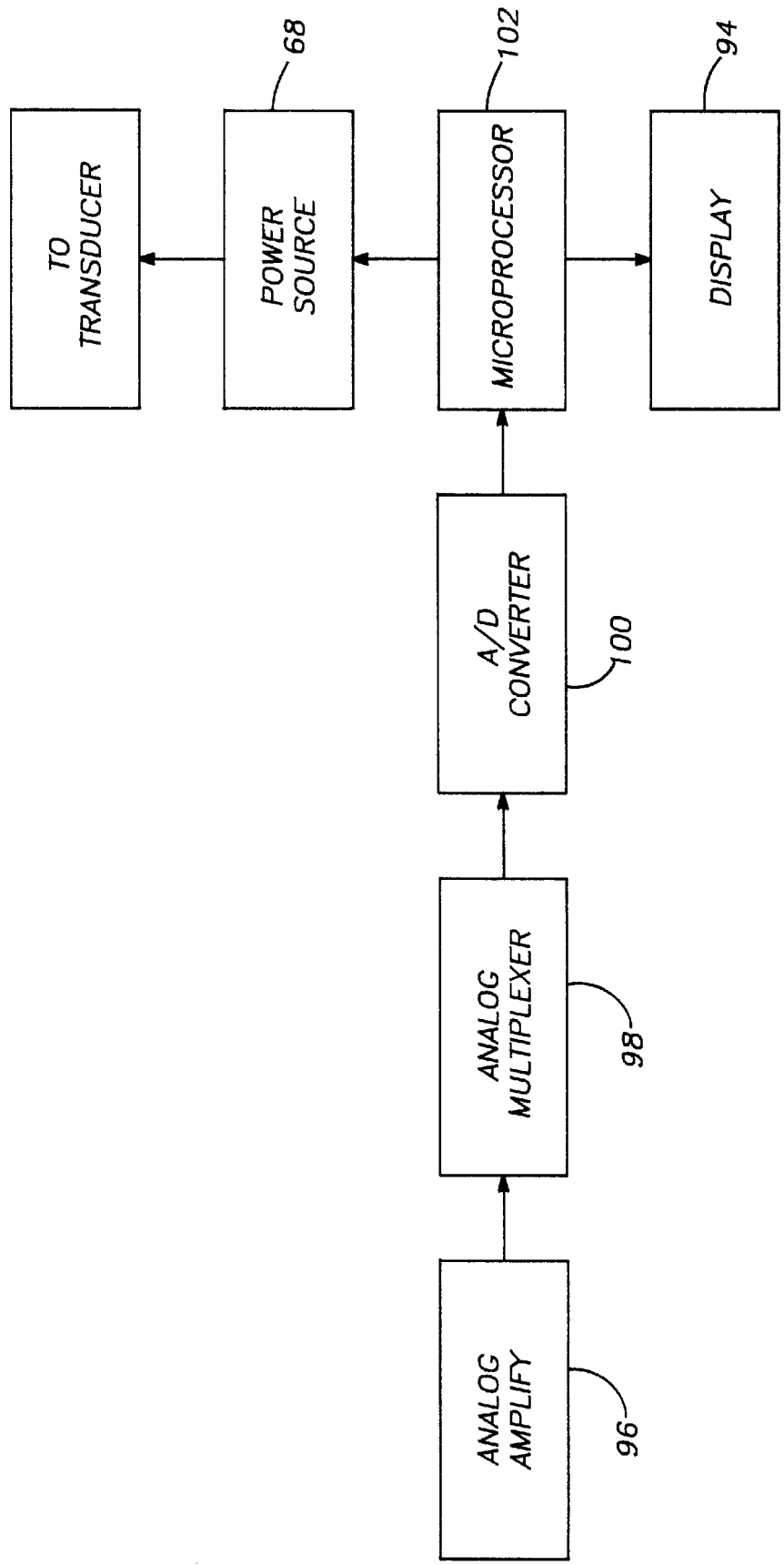

FIG. 14 is a block diagram of one embodiment of a system for processing outputs from the temperature sensors and ultrasound transducers.

DETAILED DESCRIPTION OF THE PREFERRED EMBODIMENTS

The present invention provides an apparatus to treat an anatomical structure, such as the uterus, that includes an expandable member configured to be positioned in a uterine cavity in a non-deployed state, receive an expansion media and extend to a deployed state. At least a portion of the expansion media is released through an expandable member exterior surface. Upon removal of at least a portion of the expansion from the expandable member, the expandable member contracts to a non-deployed state. An energy delivery device is coupled to the expandable member. A frame member is positionable in the interior of the expandable member. The frame member includes a first arm coupled to a second arm. The frame member has a non-deployed state and a deployed state where the first and second arms distend away from each other. Each of the, expandable member and the frame member have a non-deployed size to be introduced into the uterine cavity. A first thermal sensor member is coupled to the first arm and configured to be advanced from the first arm in the frame member expanded state into an interior of the uterus.

In another embodiment, a method for treating a uterus provides a treatment apparatus including an expandable member, an energy delivery device coupled to the expandable member, a frame member positionable in the interior of the expandable member and a first thermal sensor member coupled to the frame member. At least a portion of the expandable member is introduced into an uterine cavity. The first thermal sensor is introduced into a selected site of the uterus. Energy is delivered from the energy delivery to a selected site of the uterus and create controlled cell necrosis. The expandable member is them removed from the uterine cavity.

The method and apparatus of the present invention can be used to treat endometreosis, cancer, reversible and non-reversible sterilization, thin layer ablation, selective ablation, as an adjunctive to other therapies.

Figure 1C:
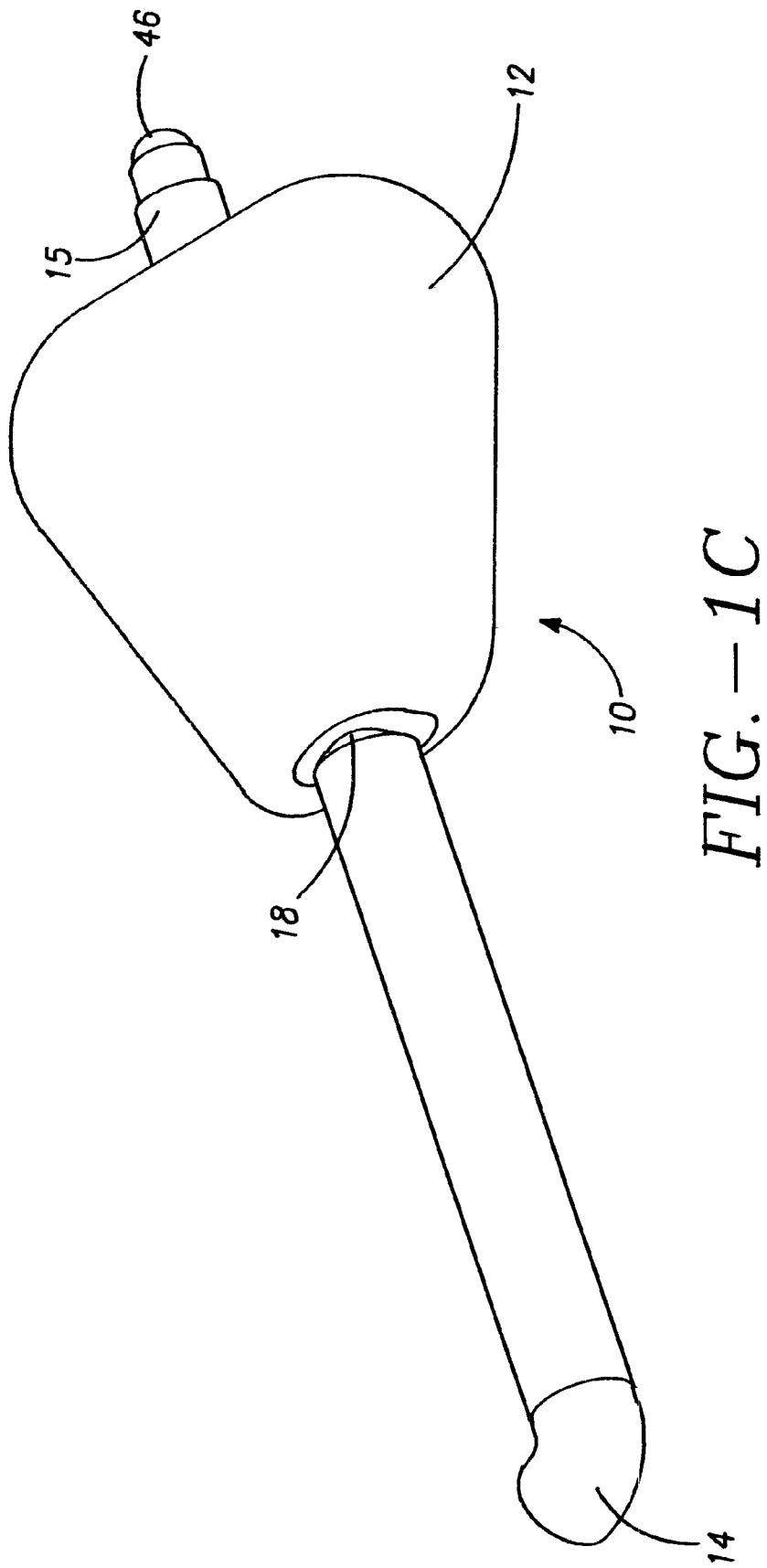
FIG. 1(c) is a perspective view of a cell necrosis apparatus of the invention in a deployed position.
Figure 2:
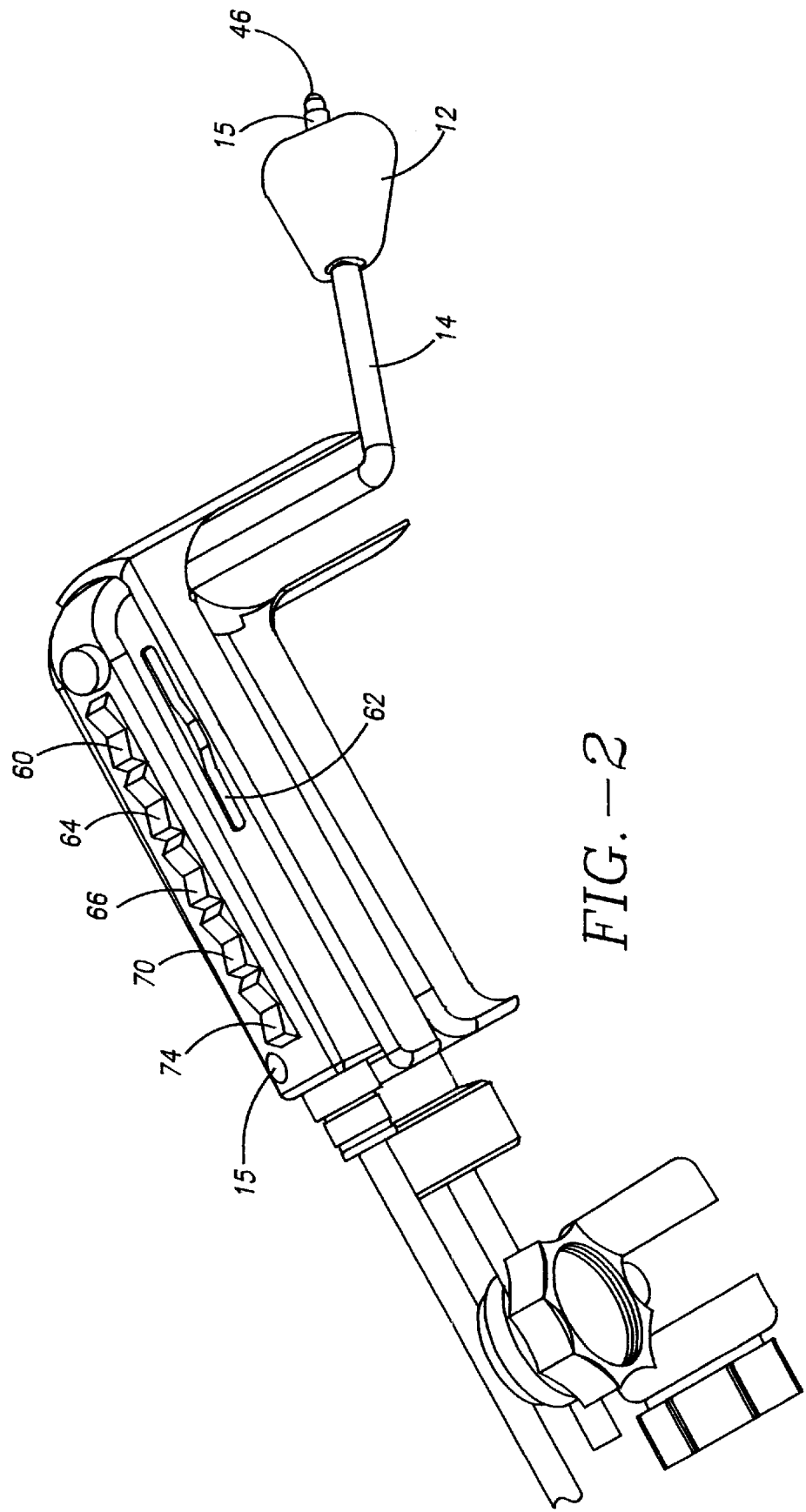
FIG. 2 is a perspective view of a handle associated with the cell necrosis apparatus of the invention.

One embodiment of cell necrosis apparatus 10 of the invention is illustrated in FIGS. 1(a), 1(b) and 1(c) and includes a porous membrane and/or an expandable member 12 that is introduced into a desired body organ or lumen through an introducer sleeve 14 which can be attached to a handpiece (handle)15 (FIG. 2). In one embodiment of the invention, expandable member 12 is a balloon, but it will be appreciated that other devices capable of being in confined non-deployed states, during their introduction into the desired body organ or lumen, and thereafter expanded to deployed states, can be utilized.

Expandable member 12 can be rolled or folded around a core lumen 16 which can contain optics, fluid paths, sensor and electronic cabling. It can be attached to a ratchet hinge 18 which imparts movement of expandable member 12 when it is in a body organ or lumen. Cell necrosis apparatus 10 can be generally rolled or folded around a helical type of elongated structure in order to provide a wringing type of motion to assist in its removal from the body organ or lumen.

Expandable member 12 is introduced through introducer sleeve 14 in a folded, or non-distended configuration. Introducer sleeve 14 can be of different cross-sectional sizes. In one embodiment, it is small enough to introduced into the cervix under local anaesthesia, and can be on the order of about 5 mm or less in diameter. Preferably, it is 3 mm or less.

Optionally positioned on handle 15 are a variety of actuators which provide physician control of cell necrosis apparatus 10, as more fully described hereafter. The actuators can be rocker switches, slider switches and the like, as are well known to those skilled in the art. Cell necrosis apparatus 10 is sufficiently opaque that it is visible under ultrasound.

Introducer sleeve 14 is introduced into the desired organ or body lumen, as shown in FIG. 1(a), with expandable member 12 in a non-deployed configuration. Following introduction, introducer sleeve 14 is withdrawn and can be retracted into handle 15. Introducer sleeve 14 can be of conventional design, such as an introducing catheter, well known to those skilled in the art. Expandable member 12 can be swept from side to side, which movement can be imparted by hinge 18. Hinge 18 also provides for easy introduction of cell necrosis apparatus 10 through the vagina, and into the cervix and uterus.

A variety of electromagnetic energy sources can be coupled to the porous membrane including, (i) an RF source coupled to an RF electrode, (ii) a coherent source of light coupled to an optical fiber, (iii) an incoherent light source coupled to an optical fiber, (iii) a heated fluid coupled to a catheter with an open channel configured to receive the heated fluid, (iv) a heated fluid coupled to a catheter with an open channel configured to receive the heated fluid, (v) a cooled fluid coupled to a catheter with a closed channel configured to receive the cooled fluid, (vi) a cooled fluid coupled to a catheter with an open channel configured to receive the cooled fluid, (vii) a cryogenic fluid, (viii) a resistive heating source, (viii) a microwave source that in one embodiment provides energy from 915 MHz to 2.45 GHz and coupled to a microwave antenna, (ix) an ultrasound source coupled to an ultrasound emitter, wherein the ultrasound source produces energy in the range of 300 KHZ to 3 GHz or (x) a microwave source.

The remainder of this disclosure is directed to the embodiment where the energy source is an RF generator and the energy delivery device is one or more RF electrodes. However, all of the other mentioned energy sources are equally applicable.

In various embodiments of the invention, the targeted cell necrosis site can be a body organ including but not limited to the uterus. It will be appreciated that the present invention is not limited to the uterus and that cell necrosis apparatus 10 can be used in other fields of medicine.

For illustration purposes, the discussion hereafter will focus on the delivery of electromagnetic energy to the uterus. Electric current flowing through the endometrium causes heating due to resistance of the tissue. Endometrial cell necrosis can be accomplished as a relatively simple medical procedure with local anesthesia to selectively treat the uterus, including but not limited to a partial or total cell necrosis of the endometrium, other uterine tissue, tumors of the uterus, including but not limited to fibroids that extend into the uterine cavity, that do not extend into the uterine cavity and those fibroids that are attached to exterior surfaces of the uterus.

Figure 3:
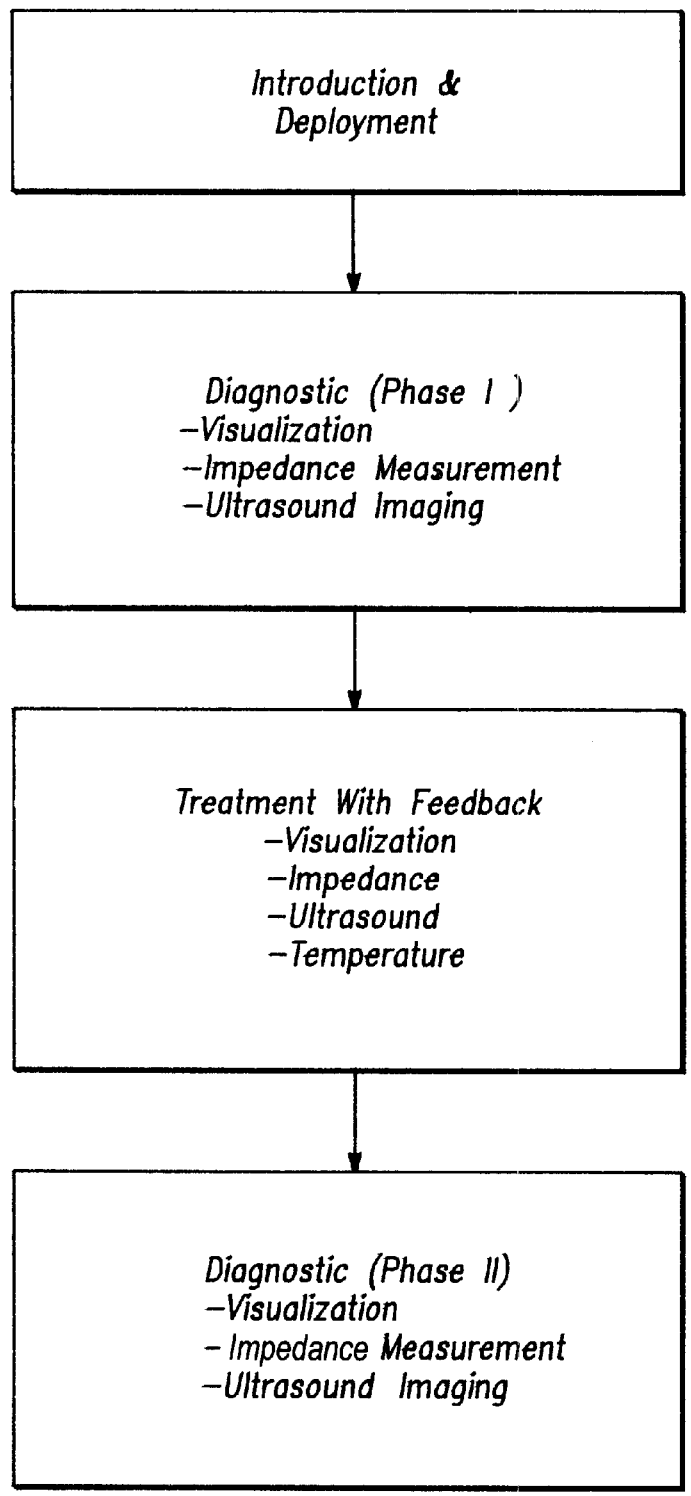
FIG. 3 is a flow chart listing the operation of the cell necrosis apparatus of the invention.

FIG. 3 is a flow chart illustrating one embodiment of the operation of cell necrosis apparatus 10. In this embodiment, cell necrosis apparatus 10 is first introduced into the uterus under local anaesthesia. Introducer sleeve 14 is then withdrawn, and expandable member 12 is expanded, either mechanically, with the introduction of a fluid or gaseous expanding medium, such as ar electrolytic solution, or a combination of both. For this purpose formed spring wires can be used alone or in combination with a fluid to expand expandable member 12. Electrolytic solution is introduced into expandable member 12, causing it to become distended and be self-retained in the uterus.

Electrolytic solution in expandable member 12 is heated to a pre-selected temperature, which can be modified and adjusted as necessary. For example, electrolytic solution can be heated and maintained at a temperature between about 60 to 90 degrees C. It can be initially introduced into expandable member 12 at the higher temperature, or it can be heated to the higher temperature in expandable member 12. By providing a heated electrolytic solution, there is a reduction in the amount of time needed to complete a satisfactory cell necrosis.

The diagnostic phase then begins. This is achieved through a variety of mechanisms, including but not limited to, (i) visualization, (ii) measuring impedance to determine the electrical conductivity between the endometrium and cell necrosis device 10 and (iii) the use of ultrasound imaging to establish a base line for the tissue to be treated.

In the treatment phase, the cell necrosis of the uterus can be conducted under feedback control. This enables cell necrosis device 10 to be positioned and retained in the uterus. Treatment can occur with minimal attention by the physician. Cell necrosis apparatus 10 automatically conforms to the interior of the uterus, provides a relatively even flow of heated electrolytic solution to assist in the cell necrosis, and a plurality of electrodes contained in zones, effectively create a flexible circuit. It can be multiplexed in order to treat the, entire endometrium or only a portion. Feedback can be included and is achieved by, (i) visualization, (ii) impedance, (iii) ultra-sound or (iv) temperature measurement. The feedback mechanism permits the turning on and off of different electrodes of the flexible circuit in a desired ablative pattern, which can be sequential from one electrode to the next, or it can jump around different electrodes. Ultrasound imaging can be used for imaging during all or a portion of the treatment phase.

The amount of cell necrosis can vary. However, it is desirable to ablate about 2 to 3 mm, with approximately 1 mm of the myometrium. Ultrasound can be used to create a map of the interior of the uterus. This information is input to a controller. Individual electrodes are multiplexed and volumetrically controlled. If desired, the area of cell necrosis can be substantially the same for each cell necrosis event.

Even though there are folds and crevices in the endometrium, the entire endometrium can be treated and selectively ablated. The selective cell necrosis may be the even penetration of RF energy to the entire endometrium, a portion of it, or applying different levels of RF energy to different endometrium sites, depending on the condition of the endometrium. The depth of RF and thermal energy penetration in the endometrium is controlled and selectable.

A second diagnostic phase may be included after the treatment is completed. This provides an indication of cell necrosis treatment success, and whether or not a second phase of treatment, to all or only a portion of the uterus, now or at some later time, should be conducted. The second diagnostic phase is accomplished through, (i) visualization, (ii) measuring impedance, (iii) ultrasound or (iv) temperature measurement.

Figure 4:
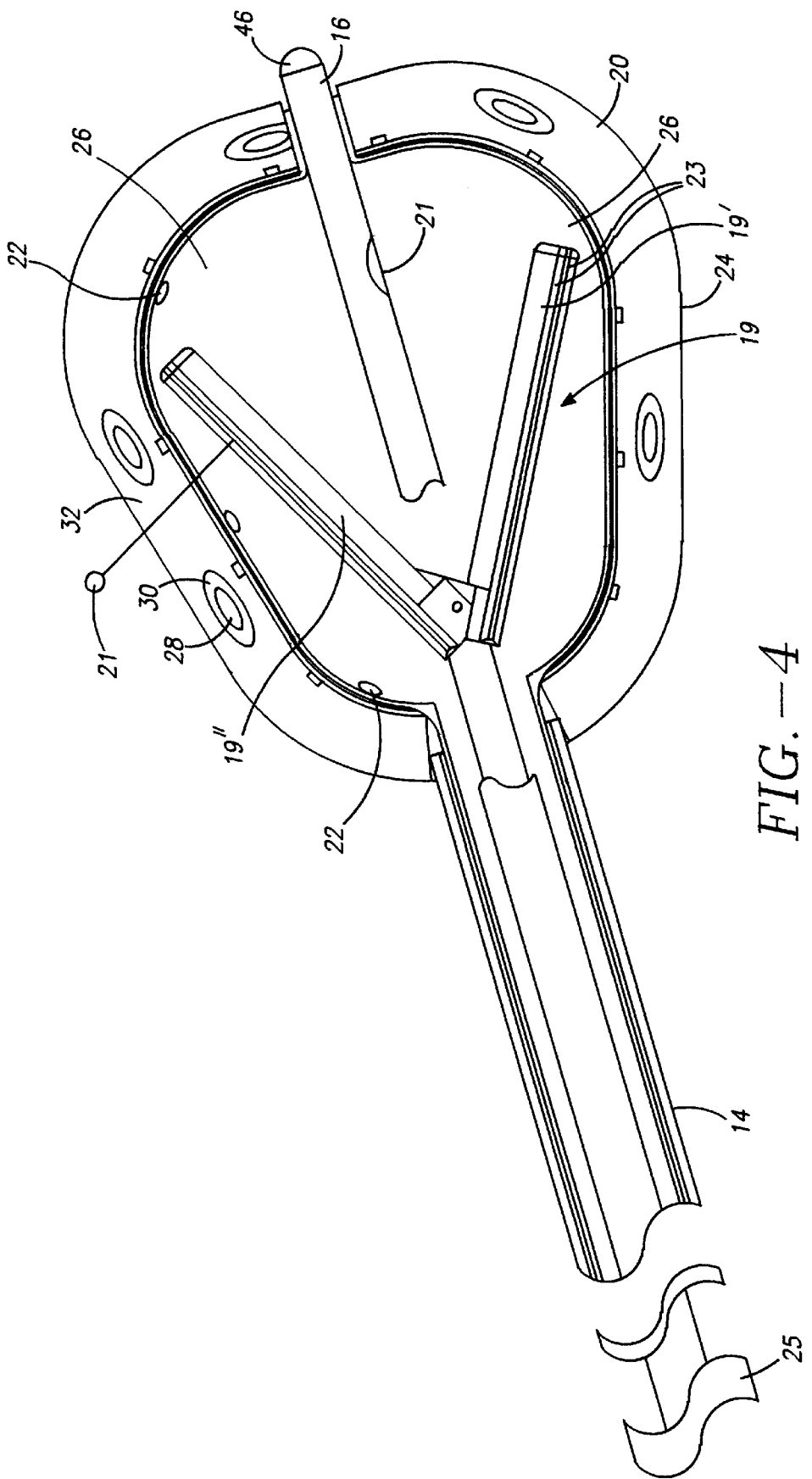
FIG. 4 is a cross-sectional view of the cell necrosis apparatus of the invention, illustrating the zone and non-zone sections of the conforming member, the frame as well as sensors and energy delivery devices coupled to the frame.
Figures 6A, 6B:
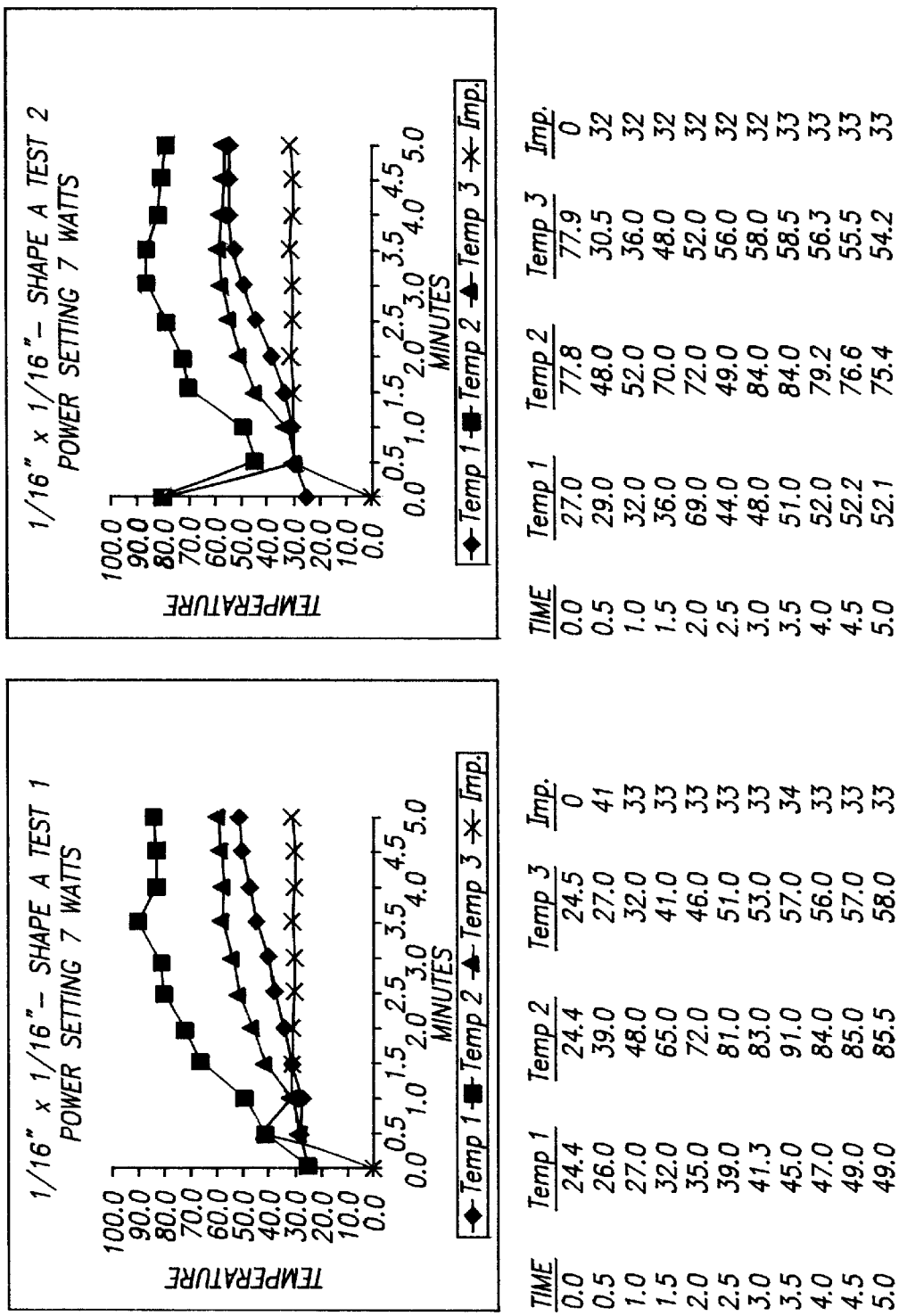
FIGS. 6(a)–6(b) are graphs and tables of measured temperatures of zone and adjacent non-zone sections of the cell necrosis apparatus illustrated in FIG. 5(a)

One embodiment of cell necrosis apparatus 10 is illustrated in FIG. 4. Expandable member 12 is made of a material that can be an insulator. For purposes of this disclosure, an insulator is a barrier to thermal or electrical energy flow. In this embodiment, expandable member 12 is substantially surrounded by a conforming member 20 which is also called a fluid conduit. Conforming member 20 receives electrolytic solution from expandable member 12, heated or not heated, through a plurality of apertures 22 formed in expandable member 12, and passes it to conforming member 20. Expandable member 12 is made of a material that permits controlled delivery of the electrolytic solution through one or more distribution ports, and can be made of a microporous material that does not include distinct apertures 22.

A frame 19 can be included in expandable member 12 and in one embodiment is used to assist opening expandable member 12 to tie deployed position. Frame can include one or more arms 19' that can be coupled together. In one embodiment, frame 19 has a deployed basket configuration that compacts to a non-deployed state in order to provide easy introduction and removal of expandable member 12 from a selected site, including but not limited to the uterine cavity. One or more sensors 21 can be coupled to frame 19 internally in a lumen or carried on an exterior surface. Sensors 21 are advanceable to and from frame 19 into a selected depth of tissue to detect the depth of cell necrosis and/or the progress of the procedure. Additionally, one or more energy delivery devices 23 can be coupled to frame 19 and advanced into a selected tissue site to create a desired amount of cell necrosis at a desired level or distance. An advancement and retraction member 25 can be coupled to sensors 21 and/or energy delivery devices 23.

In one embodiment, cell necrosis apparatus 10 conforms lightly with the interior of the uterus so that all, or almost all, of the endometrium is in contact with a conductive surface 24 of conforming member 20. Conforming member 20 is fitted into the entire uterus and expandable member 12 does not have to be moved about the uterus to complete the treatment. Alternatively, cell necrosis apparatus 10 may not entirely fill the uterus, and cell necrosis apparatus 10 is then moved about the uterus in order to ablate all of the endometrium, or those sections where cell necrosis is desired. Selected portions of the endometrium may not be ablated, such as those portions close to the fallopian tubes.

Conforming member 20 is made of a material that substantially conforms to the surface of the endometrium. This provides better conformity than the mere use of expandable member 12, and the delivery of treatment energy to the endometrium is enhanced.

While expandable member 12, with a single interior section 26, is preferred, it will be appreciated that expandable member 12 can be made of different compositions or materials, with one or more open or closed cells or chambers. The plurality of such cells or chambers can be compressed or configured in a small diameter for insertion, and are then expanded after insertion to establish the desired electrical contact with the targeted surface of the endometrium.

Conforming member 20 is made of a material that suitably conforms to a surface to be ablated, and can have a thickness in the range of about 0.01 to 2.0 cm. Conforming member 20 can be made of a foam type material. Suitable materials include but are not limited to, knitted polyester, continuous filament polyester, polyester-cellulose, rayon, polyimide, polyurethane, polyethylene, and the like. Suitable commercial foams include, (i) Opcell, available from Sentinel Products Corp., Hyannis, Mass. and (ii) UltraSorb, HT 4201 or HT 4644MD from Wilshire Contamination Control, Carlsbad, Calif. Conforming member 20 has characteristics that make it particularly moldable and formable to irregular surfaces. In one embodiment, conforming member 20 is made of a an open cell foam, or alternatively it can be a thermoplastic film such as polyurethane, low density polyethylene, or may be a silicone rubber. Additionally, conforming member 20 can be capable of extruding conductive materials from conforming member 20 itself. Conforming member 20 can be implanted with conductive ions, and conductive surface 24 can be coated with a material that improves its conductivity.

FIGS. 5(a) through 5(d) illustrate that conforming member 20 can be created by sealing two conforming members 20(a) and 20(b) together. In FIG. 5(a), conforming members 20(a) and 20(b) are sealed together between individual electrodes 28. This creates a pocket or zone 30. Zone 30 has a lower porosity for the flow of electrolytic solution than non-zone sections 32, e.g., all other sections of conforming member 20 which do not include a zone 30 with an associated electrode 28. The porosity of non-zone sections 32 is greater than the porosity of zones 30.

Electrolytic solution is released from interior 26 of expandable member 12 and passes through conforming member 20. The differences in porosity is achieved in an open cell foam, with zones 30 having less open cells than non-zone sections 30. Electrolytic solution is retained in zones 30 longer than in non-sections 32 and its temperature is elevated. The semi-trapped electrolytic solution in zones 30 combines with electrode 28 to create a large electrode. The larger electrode produces RF and thermal energy to conforming member 20, which is transferred to tissue through conductive surface 24.

Electrolytic solution travels through zones 30 at a slow enough rate to create this larger electrode effect. The porosity of zones 30 is selected so that electrolytic solution remains in the respective zone 30 sufficiently long enough to become heated to an elevated temperature and produce the larger electrode effect.

In FIG. 5(a), conforming members 20(a) and 20(b) are sealed in non-zone sections 32 and along the peripheries of conforming members 20(a) and 20(b). This creates a structure that, (i) conforms closely to the endometrium or other organ/lumen structures, (ii) effectively introduces electrolytic solution to the desired tissue site and (iii) with the inclusion of zones 30 with lower porosity, electrolytic solution is elevated to a higher temperature. The result is a greater RF and thermal effect that is evenly applied to the tissue site such as the endometrium.

FIG. 5(b) illustrates conforming members 20(a) and 20(b) sealed at electrode 28 to create zone 30, and not sealed at non-zone sections 32 except at the peripheries of conforming members 20(a) and 20(b).

FIGS. 5(c)–(d) illustrate zone 30 filled with electrolytic solution which becomes heated to a desired elevated temperature while it remains in zone 30.

As an example of cell necrosis device 10, a foam patch with zones 30 and non-zone sections 32, utilized two pieces of UltraSORB foam which were sealed between 0.004 inch by 0.016 inch (SST) flat electrode wire with approximately 80 Ω/foot. About 1.0 inch of SST wire was exposed in the foam. Different foam thickness were used and included, (i) 1/16 inch by 1/8 inch, (ii) 1/8 inch by 1/16 inch and (iii) 1/16 inch by 1/16 inch. The foam size was about 1.0 inch by 1.0 inch. A return electrode, through a sheet of brass, was utilized. A 0.9% saline solution was utilized and placed in a test bath. The presoaked foam patch was laid inside the test bath. The system was energized and temperature ac,ross the path was monitored. Temperature $T_2$ represented the temperature in the zone, while temperatures $T_1$ and $T_3$ represented temperatures in adjacent non-zone sections 32.

The results are shown in FIGS. 6(a)–(b) and 7(a)–(b). Temperatures in zone 30 were higher than temperatures in adjacent non-zone sections 32. In FIGS. 6(a)–(c), 50 Ω was connected, and the impedance was about 85 Ω. In FIG. 7(a)–(c), 50 Ω was connected, and the impedance was about 90 Ω.

Interior 26 can contain heated electrolytic solution, such as saline. The amount of electrolytic fluid in interior 26 is one of the factors for establishing the flow rate of electrolytic solution out of interior 26. Expandable member 12 can become more pressurized by increasing the amount of electrolytic solution. As electrolytic fluid enters expandable member 12, the pressure within interior 26 increases. This increases the flow rate of electrolytic solution out of apertures 22. A reduction in pressure will correspondingly reduce the flow rate. Electrolytic solution is introduced into interior 26 through fluid distribution parts formed in, for example, core lumen 16, or it can be introduced through a separate fluid conduit.

Heated electrolytic solution can be delivered from expandable member 12, through conforming member 20, and is then delivered to the tissue to be ablated. Fluid flow can be continuous or non-continuous to the tissue site.

Figure 9:
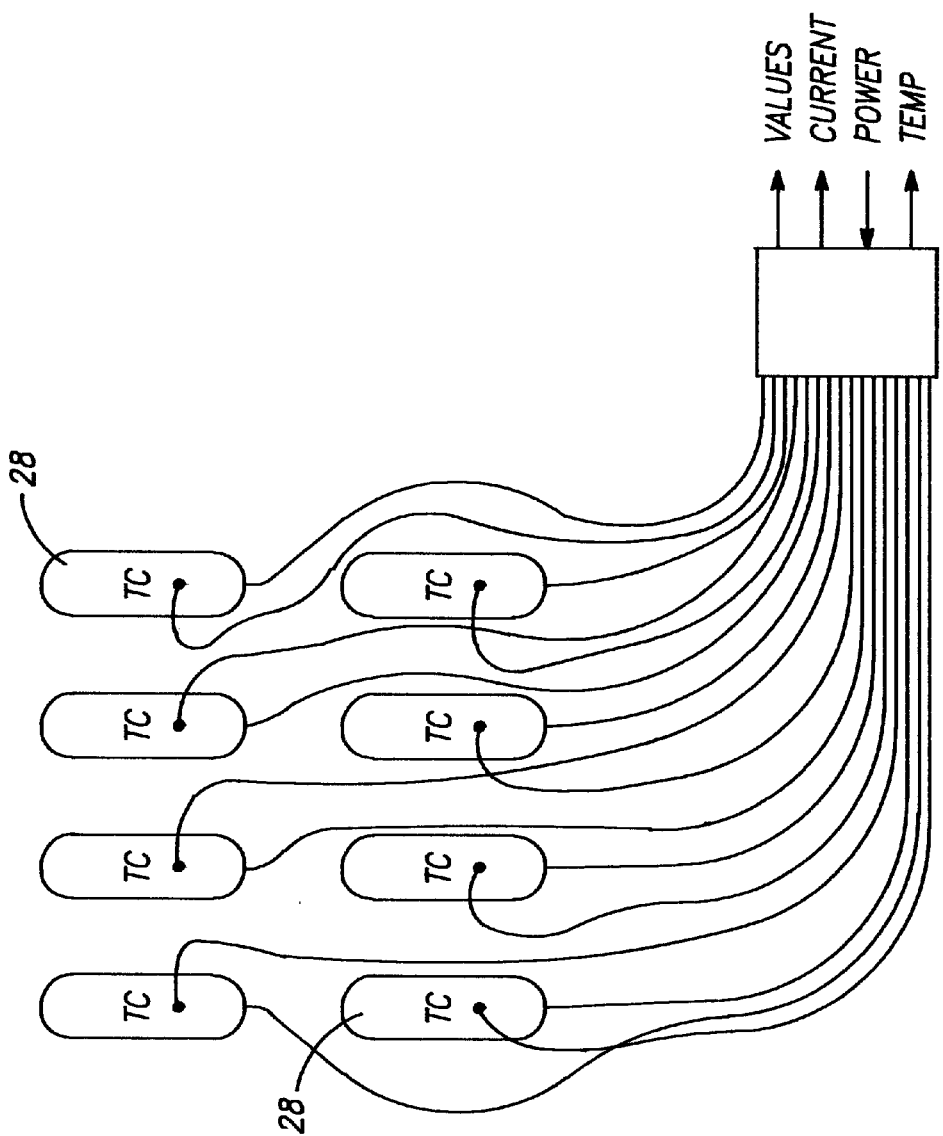
FIG. 9 is a perspective view of a plurality of electrodes that comprise a flexible circuit in the interior of the conforming member.

As shown in FIG. 8 a flexible circuit 34 is made of individual electrodes 28 in zones 30 and positioned within conforming member 20. FIG. 9 shows individual electrodes 28, with thermocouples, that can be used and multiplexed in either of monopolar or bipolar schemes.

Referring again to FIG. 8, electrodes 28 and zones 30 are capable of multiplexing so that only certain electrodes 28 deliver RF and thermal energy at a particular time period. Zones 30 provide individual ablative coverage, and delivery, for the entire conductive surface 24. In this regard, the plurality of zones 30 can provide ablative regions individually everywhere on conductive surface 24.

The selectivity can be the even application of RF energy everywhere it is applied to the endometrium so that the same depth of endometrium is ablated, or the amount of applied energy can be variable, depending on the characteristics of the endometrium surface. In this instance, certain sections of the endometrium will have more tissue ablated than other sections.

Each zone 30 connects to a separate feedwire 36, with all of the wires going to a ribbon connector 38. Feedwires 36 are insulated. Each electrode 28 and zone 30 is wired with a constantan wire in order to receive RF energy from an RF energy source. A copper wire is connected to each constantan wire. This results in the formation of a T type thermocouple "TC".

RF power can be sequentially supplied to each electrode 28, to feedwire 36 in ribbon connector 38, or it can be applied to only certain selected feedwires 36, enabling only selected electrodes 28 along with the electrolytic solution in zones 30 to deliver RF and thermal energy individually to the endometrium. In this way electrodes 28 can be multiplexed. The sizes of individual electrodes 28 are designed to provide the correct current density.

Figure 10:
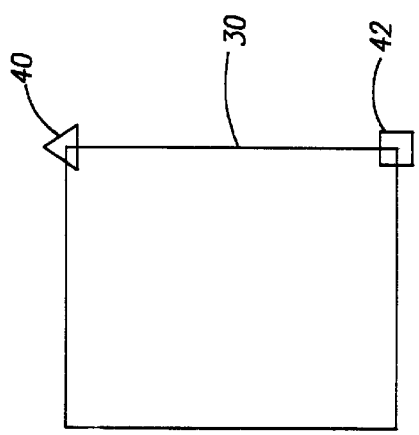
FIG. 10 is a perspective view of one of the segments of the flexible circuit shown in FIG. 8.

Referring now to FIG. 10, one or more impedance monitors 40 can be used to confirm, before an cell necrosis event, that good coupling of energy is achieved. Also included is one or more temperature monitors/sensors 42. Thermal sensors 42 are conventional thermistors or thermocouples, and are positioned adjacent to or on electrodes 28. Electrodes 28 are capable of monitoring circuit continuity. Impedance is monitored between each electrode 28 and zone 30 and a ground electrode when operated in a monopolar mode, or between electrodes 28 operating in a bipolar mode.

Figure 11:
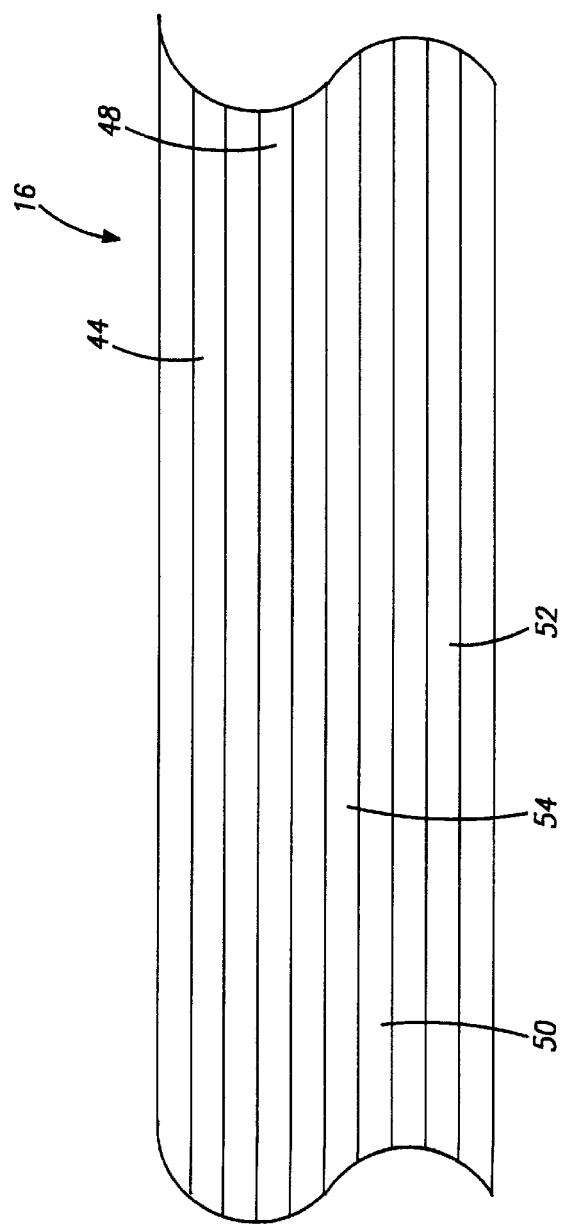
FIG. 11 is a cross-sectional view of the introducer sheath associated with the expandable member of the invention.

In FIG. 11, a cross-sectional view of core lumen 16 show,s that a variety of conduits, wires and fibers are housed in the lumen. These include, but are not limited to, viewing and illumination optical fibers 44, well known to those skilled in the art, which can deliver light, such as from a Xenon source, to viewing optics 46 (FIGS. 1(a), 1(b) and 1(c)) a tension wire 48 that connects to hinge 18; an RF cable 50 connecting feedwires 36 to an RF source; an electrolytic solution delivery conduit 52 with associated fluid distribution port; and an electrical lead 54 which couples an ultrasound energy source 56 to one or more transducers 58.

Viewing optics 46 can be a 70 degree lens, which permits a lateral field of view. Additionally, the combination of optical fibers 44 and viewing optics 21 can be in the form of a flexible viewing scope that is capable of providing a full field of view within the interior of the uterus.

A two-way valve is included with delivery conduit 52. A pump or other similar device advances electrolytic solution to and from expandable member 12 through delivery conduit 52. When the procedure is completed, electrolytic solution is removed from expandable member 12 through delivery conduit 52. Core lumen 16 is then rotated, in a twisting type of motion, in order to helically wrap the entire cell necrosis apparatus 10, e.g., expandable member 12 and conforming member 20 around core lumen 16. Substantially all of the electrolytic solution is removed. Cell necrosis apparatus 10 is then retracted back into introducer sleeve 14. It is then removed from the uterus. Alternatively, the entire cell necrosis apparatus 10 can be retracted directly into introducer sleeve 14.

Referring now to FIGS. 2 and 12, a rocker switch 60 operates the rotation and viewing of viewing optics 46, as well as the movement of the flexible scope. A slider switch 62 controls movement of introducer sleeve 14. Rocker switch 64 is associated with tension wire 48. It is activated to cause hinge 18 to pivot and impart mechanical movement to expandable member 12. Rocker switch 66 is operated by the physician to control the delivery, and in certain instances, the amount of RF energy from a suitable RF energy source 68. Rocker switch 70 controls the flow of electrolytic solution to and from expandable member 12 to an electrolytic solution source 72. Finally, a switch 74 is associated with ultrasound transducers 58. It will be appreciated that a video camera system can be associated with handle 15.

Further with regard to FIG. 12, an optical system 76 can include a light source, associated illumination and optical (imaging) fibers 44, which can be in the form of a flexible endoscope, and associated switch 60 that operates the rotation and viewing of viewing optics 44. Optical system 76 can also include an output going to a VCR, camera, and the like, and a feedback output to RF source 68 and a controller 78. RF energy source 68 can incorporate a controller, as well as both temperature and impedance monitoring devices.

Electrolytic solution source 72 can include a pump/pressure flow control device 80, as is well known to those skilled in the art. A heating device 82, for heating the electrolytic solution, is associated with electrolytic solution source 72, or it can be positioned in expandable member 12. Suitable heating, devices include but are not limited to coils, bipolar electrodes, catalysts, and other devices, as are well known to those skilled in the art. An ultrasound source 84 is coupled to one or more ultrasound transducers 58 that are positioned in or on conforming member 20. Ultrasound transducers 58 can be positioned apart from conforming member 20. An output is associated with ultrasound source 84 and RF energy source 68.

Each ultrasound transducer 58 can include a piezoelectric crystal mounted on a backing material. An ultrasound lens, fabricated on an electrically insulating material, is mounted between the piezoelectric crystal and conforming member 20. The piezoelectric crystal is connected by electrical leads 54 to ultrasound power source 86. Each ultrasound transducer 58 transmits ultrasound energy through conforming member 20 into adjacent tissue. Ultrasound transducers 58 can be in the form of an imaging probe such as Model 21362, manufactured and sold by Hewlett Packard Company, Palo Alto, Calif.

Thermal sensors 42 permit accurate determination of the surface temperature of the endometrium at conductive surface 24 adjacent to ultrasound transducers 58. Thermal sensors 42 are in thermal proximity to the piezoelectric crystals.

As previously mentioned, cell necrosis apparatus 10 can be used with a variety of different body organs or lumens including the uterus. Electrodes 28 and zones 30 can be activated to ablate the endometrium. Cell necrosis apparatus 10 can be multiplexed and deliver RF and thermal energy to only certain sections of the endometrium. Each zone 30 can provide 50 watts or less of power.

Referring now to FIG. 13, a power supply 86 feeds energy into RF power generator (source) 68 and then to cell necrosis apparatus 10). A multiplexer 88 measures current, voltage and temperature, at the numerous temperature sensors, going to each electrode 28 and zone 30 of cell necrosis apparatus 10. Electrodes 28 and zones 30 can be individually measured during an cell necrosis event at that particular sensor. Multiplexer 88 is driven by controller 78, which can be a digital or analog controller, or a computer with software. When controller 78 is a computer, it can include a CPU coupled through a system bus. This system can include a keyboard, a disk drive, or other non-volatile memory systems, a display, and other peripherals, as known in the art. Also coupled to the bus are a program memory and a data memory.

An operator interface 90 includes operator controls 92 and a display 94. Controller 78 is coupled to the imaging systems, including transducers 58, thermal sensors 42, flexible circuit 34 (current and voltage), and viewing optics 46 and optical fibers 44.

Current and voltage are used to calculate impedance. Temperature and impedance are measured and then treatment can begin. Preferably, only one electrode 28 and zone 30 ablates at a time. Diagnostics are done either optically or through ultrasound. Diagnostics can be performed both before cell necrosis of the endometrium, and also after cell necrosis as a check to ascertain the effectiveness of the treatment.

Thermal sensors 42, and sensors contained within RF energy source 68, measure voltage and current that is delivered to the endometrium. The output for these sensors is used by controller 78 to control the delivery of RF power. Controller 78 can also control temperature and power. An operator set level of power, and/or temperature, may be determined and this will not be exceeded. Controller 78 maintains the set level under changing conditions. The amount of RF and thermal energy delivered controls the amount of power. A profile of power delivered can be incorporated in controller 78, as well as a pre-set amount of energy to be delivered can also be profiled.

Feedback can be the measurement of impedance or temperature. It occurs either at controller 78, or at RF energy source 68 if it incorporated a controller. Impedance measurement can be achieved by supplying a small amount of non-therapeutic RF energy. Voltage and current are then measured to confirm electrical contact.

Circuitry, software and feedback to controller 78 result in full process control and are used to change, (i) power (modulate)—including RF, incoherent light, microwave, ultrasound and the like, (ii) the duty cycle (on-off and wattage), (iii) monopolar or bipolar energy delivery, (iv) fluid (electrolyte/saline) delivery, temperature of the fluid, flow rate and pressure and (v) determine when cell necrosis is completed through time, temperature and/or impedance. These process variables can be controlled and varied based on tissue temperature monitored at multiple sites on the ablating surface, and impedance to current flow monitored at each electrode 28 and zone 30, indicating changes in current carrying capability of the tissue during the ablative process. Additionally, controller 78 can provide multiplexing, monitor circuit continuity, and/or determine which electrode 28 and zone 30 is activated.

A block diagram of one embodiment of suitable processing circuitry is shown in FIG. 14. Thermal sensors 42 and transducers 58 are connected to the input of an analog amplifier 96. Thermal sensors 42 can be thermistors which have a resistance that varies with temperature. Analog amplifier 96 can be a conventional differential amplifier circuit for use with thermistors and transducers. The output of analog amplifier is sequentially connected by an analog multiplexer 98 to the input of an analog to digital converter 100. The output cf amplifier 96 is a voltage which represents the respective sensed temperatures. The digitized amplifier output voltages are supplied by analog to digital converter 100 to a microprocessor 102. Microprocessor 102 calculates the temperature or impedance of the tissue. Microprocessor 102 can be a type 68000. However, it will be appreciated that any suitable microprocessor, or general purpose digital or analog computer, can be used to calculate impedance or temperature.

Microprocessor 102 sequentially receives and stores digital representations of impedance and temperature at electrodes 28 and zones 30. Each digital value received by microprocessor 102 corresponds to different temperatures and impedances.

Calculated temperature and impedance values can be indicated on display 94. Alternatively, or in additional to the numerical indication of temperature or impedance, calculated impedance and temperature values can be compared by microprocessor 102 with temperature and impedance limits. When the values exceed predetermined temperature or impedance values, a warning can be given on display 94, and additionally, the delivery of RF energy to that electrode 28 and zone 30 is then multiplexed to another electrode 28 and zone 30. A control signal from microprocessor 102 can reduce the power level supplied by RF power source 68, or deenergize the power delivered to a particular electrode 28 and zone 30.

Thus, controller 78 receives and stores the digital values which represent temperatures and impedances sensed. Calculated surface temperatures and impedances can be forwarded by controller 78 to display 94. If desired, the calculated surface temperature of the endometrium is compared with a temperature limit, and a warning signal can be sent to display 94. Similarly, a control signal can be sent to RF energy source 68 when temperature or impedance values exceed a predetermined level.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be delined by the following claims and their equivalents.

What is claimed is:

1. An apparatus to treat a uterus, comprising:
   an expandable member configured to be positioned in a uterine cavity in a non-deployed state, receive an expansion media and extend to a deployed state, release at least a portion of the expansion media through an expandable member exterior surface and upon a removal of at least a portion of the expansion media contract to a non-deployed state;
   an energy delivery device coupled to the expandable member;
   a frame member positionable in the interior of the expandable member and having a non-deployed state and a deployed state, the expandable member and the frame member each having a size in the non-deployed states to be introducable into the uterine cavity; and
   a first thermal sensor member coupled to and advanceable from the frame into a selected site of the uterus.

2. The apparatus of claim 1, wherein the frame member is a structural frame positioned in the expandable member.

3. The apparatus of claim 1, wherein the frame includes a first arm and a second arm that distend away from each other in the frame deployed state.

4. The apparatus of claim 3, further comprising:
   a second thermal sensor coupled to the second arm and configured to be advanced from the second arm in the frame member expanded state into a selected site of the uterus.

5. The apparatus of claim 3, further comprising:
   a first advanceable energy delivery device coupled to and advanceable from the first arm, the first advanceable energy delivery device including a tissue piercing distal portion.

6. The apparatus of claim 5, further comprising:
   a second advanceable energy delivery device coupled to and advanceable from the second arm, the second advanceable energy delivery device including a tissue piercing distal portion.

7. The apparatus of claim 5, further comprising:
   a first insulation sleeve positionable around an exterior of the first advanceable energy delivery device, the first insulation sleeve having a tissue piercing distal portion.

8. The apparatus of claim 6, further comprising:
   a first insulation sleeve positionable around an exterior of the first advanceable energy delivery device, the first insulation sleeve having a tissue piercing distal portion; and
   a second insulation sleeve positionable around an exterior of the second advanceable energy delivery device, the second insulation sleeve having a tissue piercing distal portion.

9. The apparatus of claim 6, further comprising:
   a second sensor coupled to a distal portion of the second advanceable energy delivery device; and wherein the first sensor is coupled to a distal portion of the first advanceable energy delivery device.

10. The apparatus of claim 9, further comprising:
    a membrane positioned at an exterior surface of the expandable member, the membrane configured to receive at least a portion of the expansion media and deliver the expansion media to at least a portion of a uterine cavity surface.

11. The apparatus of claim 10, wherein the expansion media is an electrolytic solution.

12. The apparatus of claim 3, wherein the energy delivery device includes a plurality of RF electrodes.

13. The apparatus of claim 12, further comprising:
    a second thermal sensor coupled to the second arm and configured to be advanced from the second arm in the frame member expanded state into an interior of the uterus.

14. The apparatus of claim 13, further comprising:
    a first advanceable energy delivery device coupled to and advanceable from the first arm, the first advanceable energy delivery device including a tissue piercing distal portion; and
    a second advanceable energy delivery device coupled to and advanceable from the second arm, the second advanceable energy delivery device including a tissue piercing distal portion.

15. The apparatus of claim 14, further comprising:
    a membrane positioned at an exterior surface of the expandable member, the membrane configured to receive at least a portion of the expansion media and deliver the expansion media to at least a portion of a uterine cavity surface.

16. The apparatus of claim 15, further comprising:
    a first insulation sleeve positionable around an exterior of the first advanceable energy delivery device, the first insulation sleeve having a tissue piercing distal portion; and
    a second insulation sleeve positionable around an exterior of the second advanceable energy delivery device, the second insulation sleeve having a tissue piercing distal portion.

17. The apparatus of claim 1, wherein the expansion media is an electrolytic solution.

18. The apparatus of claim 17, wherein the electrolytic solution is a saline solution.

19. The apparatus of claim 1, further comprising:
    a membrane positioned at an exterior surface of the expandable member, the membrane configured to receive at least a portion of the expansion media and deliver the expansion media to at least a portion of a uterine cavity surface.

20. The apparatus of claim 19, wherein the expansion media is an electrolytic solution.

21. The apparatus of claim 1, wherein the expandable member is a balloon.

22. The apparatus of claim 21, wherein the balloon is at least partially porous.

23. The apparatus of claim 1, further comprising:
    an elongated member coupled to the expandable member.

24. The apparatus of claim 23, wherein the elongated member is an introducer.

25. The apparatus of claim 1, wherein the energy delivery device includes a plurality of RF electrodes.

26. The apparatus of claim 1, wherein the energy delivery device includes an optical fiber configured to be coupled to a laser.

27. The apparatus of claim 1, wherein the energy delivery device includes a heated fluid.

28. The apparatus of claim 1, wherein the energy delivery device includes a cooled fluid.

29. The apparatus of claim 1, wherein the energy delivery device includes a cryogenic fluid.

30. The apparatus of claim 1, wherein the energy delivery device includes a resistive heating source.

31. The apparatus of claim 1, wherein the energy delivery device includes a microwave antenna.

32. The apparatus of claim 1, wherein the energy source includes an ultrasound transducer.

33. The apparatus of claim 1, wherein the energy delivery device includes a plurality of energy delivery members coupled to the expandable member.

34. The apparatus of claim 1, wherein the energy delivery device includes a plurality of energy delivery members positioned on an exterior surface of the expandable member.

35. The apparatus of claim 1, further including:
a membrane positioned at an exterior surface of the expandable member, the membrane configured to receive at least a portion of the expansion media and deliver the expansion media to at least a portion of a uterine cavity surface.

36. The apparatus of claim 35, wherein the energy delivery device includes a plurality of energy delivery members coupled to the membrane.

37. A method for treating a uterus, comprising:
providing a treatment apparatus including an expandable member, an energy delivery device coupled to the expandable member, a frame member positionable in the interior of the expandable member and a first thermal sensor coupled to the frame member;
introducing at least a portion of the expandable member into a uterine cavity;
introducing the first thermal sensor into a selected site of the uterus;
delivering energy from the energy delivery device to at least a portion of the uterus;
controllably creating cell necrosis in at least a portion of the uterus; and
removing the expandable member from the uterine cavity.

38. The method of claim 37, further comprising:
introducing an expansion medium into the expandable member after the at least portion of the expandable member is position in the uterine cavity.

39. The method of claim 37, further comprising:
introducing an electrolytic solution into the expandable member after the at least portion of the expandable member is positioned in the uterine cavity.

40. The method of claim 39, wherein the electrolytic solution receives energy from the energy delivery device and delivers energy to the uterus and create a controlled cell necrosis.

41. The method of claim 37, wherein at least a portion of an endometrium layer is ablated.

42. The method of claim 37, wherein substantially all of an endometrium layer is ablated.

43. The method of claim 37, wherein at least a portion of a fibroid is ablated.

44. The method of claim 43, wherein at least a portion of the fibroid extends into the uterine cavity.

45. The method of claim 43, wherein the fibroid is located in the uterus below an endometrium layer.

46. The method of claim 37, wherein the apparatus further includes, a membrane positioned at an exterior surface of the expandable member, the membrane configured to receive at least a portion of an electrolytic solution from an interior of the expandable member.

47. The method of claim 37, wherein the energy delivery device includes an optical fiber configured to be coupled to a laser.

48. The method of claim 37, wherein the energy delivery device includes a heated fluid.

49. The method of claim 37, wherein the energy delivery device includes a cooled fluid.

50. The method of claim 37, wherein the energy delivery device includes a cryogenic fluid.

51. The method of claim 37, wherein the energy delivery device includes a resistive heating source.

52. The method of claim 37, wherein the energy delivery device includes a microwave antenna.

53. The method of claim 37, wherein the energy source includes an ultrasound transducer.

* * * * *